US006659142B2

(12) United States Patent
Downs et al.

(10) Patent No.: US 6,659,142 B2
(45) Date of Patent: Dec. 9, 2003

(54) APPARATUS AND METHOD FOR PREPARING FLUID MIXTURES

(75) Inventors: Robert Charles Downs, La Jolla, CA (US); Mark Richard Weselak, San Diego, CA (US)

(73) Assignee: IRM, LLC, Hamilton (BM)

( * ) Notice: Subject to any disclaimer, the term of this patent is extended or adjusted under 35 U.S.C. 154(b) by 16 days.

(21) Appl. No.: 09/818,748

(22) Filed: Mar. 27, 2001

(65) Prior Publication Data

US 2002/0139439 A1 Oct. 3, 2002

(51) Int. Cl.[7] .................................................. B65B 3/04
(52) U.S. Cl. ........................... 141/9; 141/2; 141/101; 141/181; 141/237; 141/270; 141/284; 73/864.17; 422/100
(58) Field of Search ........................ 141/2, 9, 99, 100, 141/101, 104, 129, 130, 135, 153, 163, 181, 192, 198, 234, 237, 270, 283, 284; 73/864.17, 864.16, 864.13; 422/63, 65, 81, 99, 100, 104

(56) References Cited

U.S. PATENT DOCUMENTS

| 5,306,510 A | 4/1994 | Meltzer |
| 5,736,105 A | 4/1998 | Astle |
| 5,738,728 A | 4/1998 | Tisone |
| 5,741,554 A | 4/1998 | Tisone |
| 5,743,960 A | 4/1998 | Tisone |
| 5,916,524 A | 6/1999 | Tisone |
| 6,039,211 A | 3/2000 | Slater et al. |
| 6,063,339 A | 5/2000 | Tisone et al. |
| 6,296,673 B1 | 10/2001 | Santarsiero et al. |

FOREIGN PATENT DOCUMENTS

| WO | WO 00/78445 | 12/2000 |
| WO | WO 02/062484 A1 | 8/2002 |
| WO | WO 02/063027 A1 | 8/2002 |
| WO | WO 02/068157 A2 | 9/2002 |
| WO | WO 02/075277 A2 | 9/2002 |

Primary Examiner—Timothy L. Maust
(74) Attorney, Agent, or Firm—Timothy L. Smith; Christopher C. Sappenfield; Quine Intellectual Property Law Group, P.C.

(57) ABSTRACT

A system and method for preparing and dispensing fluid mixtures is provided. Fluid wells are positioned below a plurality of fluid dispensing devices, such as syringes configured to dispense fluid into the individual fluid wells. The fluid dispensing devices are configured to be positionable relative the fluid wells to enable different fluid dispensers to be sequentially positionable over a particular fluid well. A controller controls the relative movement between fluid wells and the fluid dispensing devices. In a preferred embodiment, the controller selectively moves multi-well vessels in one direction and moves the fluid dispensing devices in a second direction so that when directed by the controller, a selected fluid dispensing device is enabled to deposit a determined quantity of a fluid into a selected individual well of the multi-well vessels.

60 Claims, 6 Drawing Sheets

APPARATUS AND METHOD FOR PREPARING FLUID MIXTURES

FIELD OF THE INVENTION

The present invention relates to the field of fluid dispensing systems. In particular, the present invention relates to an automated and robotic system for providing repeatable, high throughput dispensing of a plurality of fluids.

BACKGROUND OF THE INVENTION

Fluid dispensing systems are useful in a variety of areas, including the area of preparing fluid mixture samples to be screened for identification of a fluid mixture capable of crystallizing a protein that is, in turn, studied with x-rays to determine its function and the function of the gene encoding it.

With the identification of the more than 31,000 genes of the human genome, the determination of each gene's role in the functioning of the human body has become of paramount importance. Genes generally function to produce at least one protein, and thus the functions of numerous proteins produced by genes also are studied. Ascertaining protein structure can be an important step in understanding the function of that protein.

One technique for ascertaining a protein's structure is to obtain high-quality x-rays of the protein's crystalline structure. To do so, a preliminary step is crystallizing the protein. One technique for protein crystallization involves crystallizing the protein in a fluid mixture formulated to provide a stable crystal structure for that particular protein. Growing protein crystals using such a technique, however, can be difficult and very time consuming. Each new protein crystallization typically requires a unique concentration and mixture of fluids for crystal growth. It can be necessary to screen a protein sample against hundreds or even thousands of available fluid mixtures in order to determine a proper fluid mixture that will crystallize a single protein. For example, finding the proper fluid mixture may require varying the composition of the mixture using a multi-dimensional array of variables, such as different salt and buffer fluids, different concentrations and pH values for each fluid, and different atmospheric conditions.

Screens for suitable protein crystallization conditions are currently conducted manually using skilled technicians. Performing each screen can be a labor intensive process in part because the different fluids into which the proteins are deposited must themselves be deposited in very small amounts into very small fluid reservoirs. The physical act of dispensing such small amounts into such small fluid reservoirs is itself a time consuming and inaccurate process. In addition, the amount of protein available for each individual screen is often limited, and screening fluids used in each screen are typically measured in microliters. This requires a high level of precision and accuracy that can be difficult even for skilled technicians. Reliability and repeatability of each screen is integral to the precision and accuracy of each screen. Accordingly, there exists a need to automate the screening process, and to increase the level of precision, accuracy and repeatability of the process.

Conventional crystallization techniques may require that each protein to be crystallized is screened against numerous different fluid mixtures (typically hundreds, or many thousand) in order to find a proper composition that provides stable crystallization conditions for the particular protein in question. In a manual screening process, a technician is primarily responsible for measuring, mixing, and dispensing each unique fluid mixture. Such a manual process is time consuming and expensive, and therefore the variations of fluid mixtures are often limited because of time constraints in the screening process. Unfortunately, by reducing the granularity of the screen, a less than optimum fluid mixture will likely be selected. Further, such a manual screening process is highly susceptible to human mathematical and measurement errors in fluid preparation. In such a manner, the screen may produce erroneous, unreliable, or unrepeatable results.

Yet another problem associated with screening crystallization conditions is that many of the known buffer fluids, and other fluids used in the screens tend to be highly volatile. These volatile fluids can evaporate or change in character over time. Therefore, it can be difficult to manually prepare a screen having a large number of individual tests because of the time required to deposit the fluids into each well. As the different fluids are deposited in each well, the volatile fluids can evaporate or otherwise change composition, rendering the particular screen inaccurate.

Therefore, there exists a need for a fluid dispensing system that can quickly and repeatedly perform the multiple fluid depositing steps required for large numbers of screens or other types of precise, highly repeated, fluid handling processes.

SUMMARY OF THE INVENTION

The present invention alleviates to a great extent the disadvantages of the known protein crystallization and screening techniques by providing an automated system and method of performing multiple fluid depositing steps for high throughput processing protein screening and crystallization.

Briefly, in a preferred embodiment, fluid wells are positioned below a plurality of fluid dispensing devices. For example, syringes may be configured to dispense fluid into the individual fluid wells. The fluid dispensing devices are configured to be positionable relative the fluid wells. This enables different fluid dispensers to be sequentially positionable over a particular fluid well. A controller preferably controls the relative movement between the fluid wells and the fluid dispensing devices. It is preferred that the controller include software that allows operator flexibility in determining the relative movement between the fluid wells and the fluid dispensing devices.

In operation, the controller selectively operates a multi-well vessel transport in one direction and moves the fluid dispensing devices in a second direction. When directed by the controller, a selected fluid dispensing device deposits a determined quantity of a fluid into a selected individual well of the appropriate multi-well vessel.

It is preferred that a plurality of multi-well vessels and fluid dispensing devices be arranged to work in close association with each other so that an increase in throughput is achieved. Accompanying the increase in throughput is an increase in reliability and repeatability, and a decrease in the time associated with fluid deposition. The increased throughput substantially eliminates the conventional problem of having the character of the deposited fluids change as a result of volatility.

In one aspect the present invention features an apparatus for automatically preparing mixtures of fluids in a plurality (e.g., 96, 384, or 1536) of wells of a multi-well holder. The apparatus includes a plurality of fluid dispensing devices capable of being sequentially positioned above the wells.

Each fluid dispensing device is capable of dispensing a fluid into a well when the well is positioned below the fluid dispensing device. The apparatus also includes a controller that controls dispensation of the fluid from the fluid dispensing devices and the relative movement between the fluid dispensing devices and the wells.

In preferred embodiments, the plurality of tubes are configured so that 1, 2, 3, 4, 5, 6, 7 or 8 multi-well holders can be beneath the plurality of tubes at the same time. Preferably, the plurality of tubes are configured so that the dispensing mechanisms can deliver the material to 1, 2, 3, 4, 5, 6, 7 or 8 multi-well holders at the same time. The plurality of tubes may be configured so that all of the dispensing mechanisms can deliver the material at the same time. In one preferred embodiment, the moving element has a length of at least n multi-well plates, wherein n is the number of multi-well plates, wherein each multi-well plate has m wells, wherein m is the number of wells, wherein the apparatus processes a multi-well plate every m dispensings even though the multi-well plate is in the apparatus for n times m dispensings. For example, the moving element has a length of at least five multi-well plates, wherein each multi-well plate has 96 wells, wherein the apparatus processes a multi-well plate every 96 dispensings, even though the multi-well plate is in the apparatus for 480 dispensings. The dispensor controller preferably directs the delivery of the material from each fluid container to each multi-well plate, for example the dispensor controller may direct the delivery of the material from each of at least eight fluid containers to each of at least five multi-well plates.

In another aspect, the invention features a system for efficiently loading mother liquors in a plurality of multi-well sample plates for a course screen, the plurality of sample plates arranged with corresponding columns aligned, the system including: (a) a plate arranging area configured to receive the plurality of sample plates; (b) a plurality of fluid containers, each fluid container holding a predetermined mother liquor mixture; (c) a plurality of syringes arranged in an array, the array, each syringe being in fluid communication with an associated one of the fluid containers; (d) a drive mechanism constructed to sequentially position the syringes in the array directly over each column of wells in the sample plate; (e) a dispensing mechanism associated with each syringe; and (f) a fluid controller communicating to the dispensing mechanism; wherein the fluid controller directs the dispensing mechanisms to deliver a quantity of each associated mother liquor into each sample well in a column before the drive mechanism moves the syringe array to a next column.

In preferred embodiments the plurality of syringes are configured so that 1, 2, 3, 4, 5, 6, 7 or 8 sample plates can be beneath the plurality of syringes at the same time. The plurality of syringes preferably are configured so that the dispensing mechanisms can deliver the material to 1, 2, 3, 4, 5, 6, 7 or 8 sample plates at the same time. The plurality of syringes may be configured so that all of the dispensing mechanisms can deliver the material at the same time. In one preferred embodiment, the system includes a moving element that has a length of at least n sample plates, wherein n is the number of sample plates, wherein each sample plate has m wells, wherein m is the number of wells, wherein the system processes a sample plate every m dispensings even though the sample plate is in the system for n times m dispensings. For example, the moving element has a length of at least five sample plates, wherein each sample plate has 96 wells, wherein the system processes a sample plate every 96 dispensings, even though the sample plate is in the system for 480 dispensings. The fluid controller preferably directs the delivery of the material from each fluid container to each sample plate, for example, the dispensor controller directs the delivery of the material from each of at least eight fluid containers to each of at least five multi-well plates.

In another aspect, the present invention provides a method for automatically preparing a mixture in a well of a multi-well holder. The method involves the steps of: (a) moving the multi-well holder so that the well is positioned below a fluid dispensing device; (b) dispensing fluid from the fluid dispensing device into the well; and (c) repeatedly moving the multi-well holder so that the well is positioned below a next fluid dispensing device and dispensing fluid from the next fluid dispensing device into the well until a predetermined mixture is prepared.

In preferred embodiments, the plurality of syringes are configured so that 1, 2, 3, 4, 5, 6, 7 or 8 multi-well holders can be beneath the plurality of syringes at the same time. The plurality of syringes preferably are configured so that the syringes can deliver the material to 1, 2, 3, 4, 5, 6, 7 or 8 multi-well holders at the same time. The plurality of syringes may be configured so that all of the syringes can deliver the material at the same time. In one preferred embodiment, the sample plates are on a moving element that has a length of at least n sample plates, wherein n is the number of multi-well plates, wherein each multi-well plate has m wells, wherein m is the number of wells, wherein the method processes a multi-well plate every m dispensings even though the method involves n times m dispensings. For example, the sample plates are on a moving element that has a length of at least five multi-well plates, wherein each multi-well plate has 96 wells, wherein the method processes a multi-well plate every 96 dispensings, even though the method involves 480 dispensings. Preferably, a controller directs the delivery of the material from one or more fluid containers to each sample plate. For example, the controller directs the delivery of the material from each of at least eight fluid containers to each of at least five multi-well plates.

Finally, in another aspect, the present invention provides a syringe array for dispensing liquid into a plurality of multi-well sample plates. The syringe array includes a plurality of N syringes coupled into a linear array. N is a whole number multiple of the number of sample wells in one line of each sample well. Each sample plate includes sample wells organized in a geometric pattern. The line may be a row or a column. By way of example, the number of sample wells in a line may be 12 and N may be 96.

In preferred embodiments of any of the aspects of the invention described herein, the footprint of the tubes in the column direction (i.e., the column length footprint) of the multi-well holder is at least 5.030, 10.060, 15.090, 20.120, 25.150, 30.180, 35.210, 40.240, or 45.270 inches long.

It readily will be appreciated that an advantage of the present system is to increase the speed, accuracy and reliability of protein crystallization and processing operations.

BRIEF DESCRIPTION OF THE DRAWINGS

These and other features and advantages of the present invention will be appreciated from review of the following detailed description of the invention, along with the accompanying figures in which like reference numerals refer to like parts throughout.

Some or all of the Figures may be schematic representations for purposes of illustration and do not necessarily depict the actual relative sizes or locations of the elements shown.

DETAILED DESCRIPTION OF THE INVENTION

In the following paragraphs, the present invention will be described in detail by way of example with reference to the drawings. Throughout this description, the preferred embodiments and examples do not limit the scope of the present invention.

I. A Multi-Fluid Dispensing System

Figure 1:
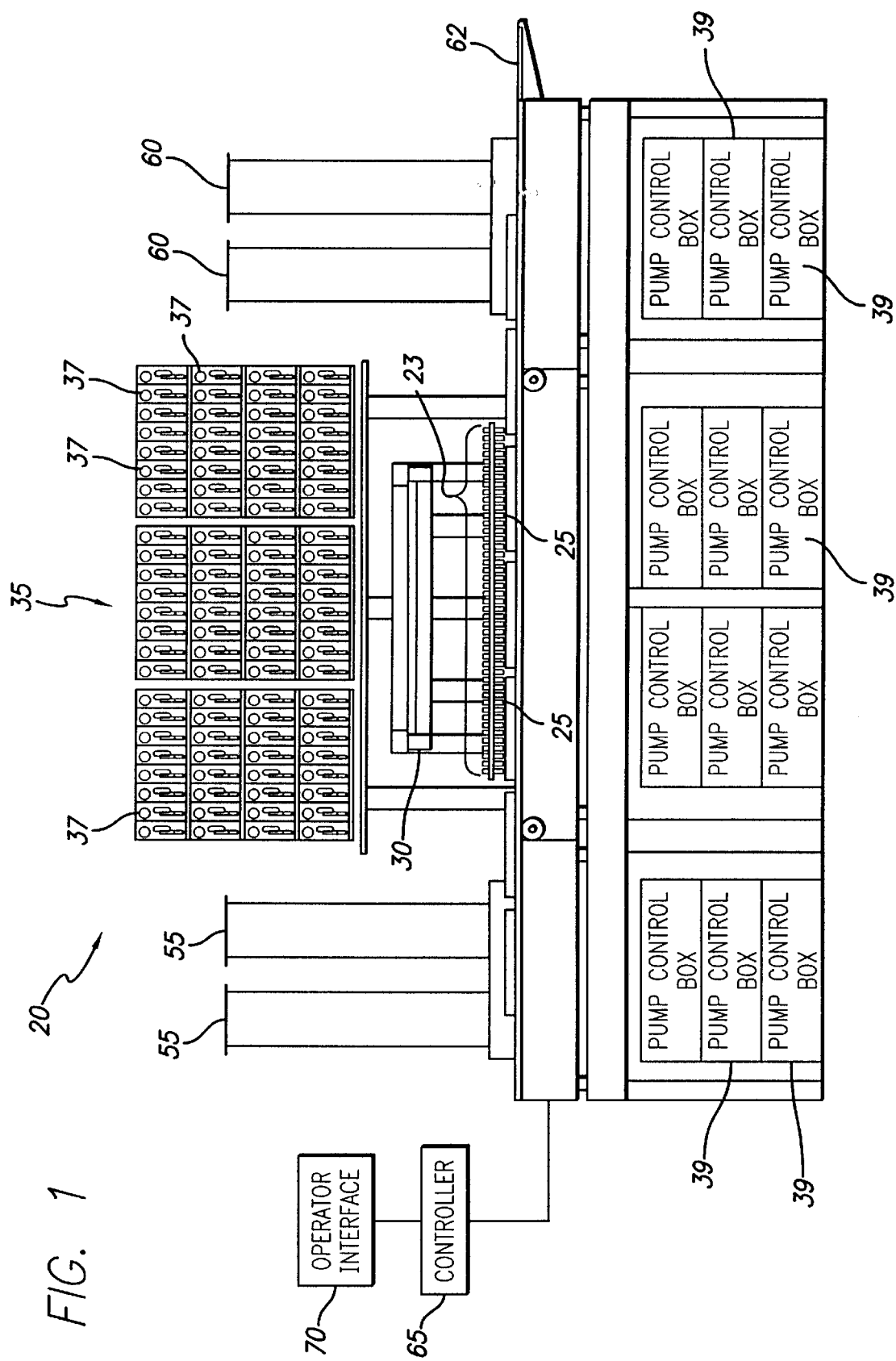
FIG. 1 is an elevation of a fluid dispensing system in accordance with the present invention.

Referring now to FIG. 1, an apparatus for preparing a fluid mixture is shown. More particularly, the apparatus for preparing a fluid mixture is illustrated as a multi-fluid dispensing system 20. The multi-fluid dispensing system 20 provides an automated and robotic process for handling, dispensing and storing fluid samples. The fluid samples may be, for example, genetic material, chemicals, or living cells. In one embodiment, the fluids may be "mother liquors" for the growth of protein crystals. Other types of fluids can be employed in the present invention. Although the illustrated examples are used to prepare fluid mixtures for screening protein crystallization mixtures, the apparatus and method for preparing fluid mixtures may be used for other purposes and in other fields.

The multi-fluid dispensing system 20 comprises a plurality of fluid dispensing tubes 25 mounted in a tube array 23. The tube array is attached to a tube transport 30. In one embodiment, 96 tubes 25 are mounted to the tube array 23 in a single row. Different numbers of tubes 25 mounted in a different arrangement on the tube array 23 can be employed. For example, shown in FIG. 4, a plurality of tubes 25 are mounted in a staggered configuration on tube array 23.

Figure 2:
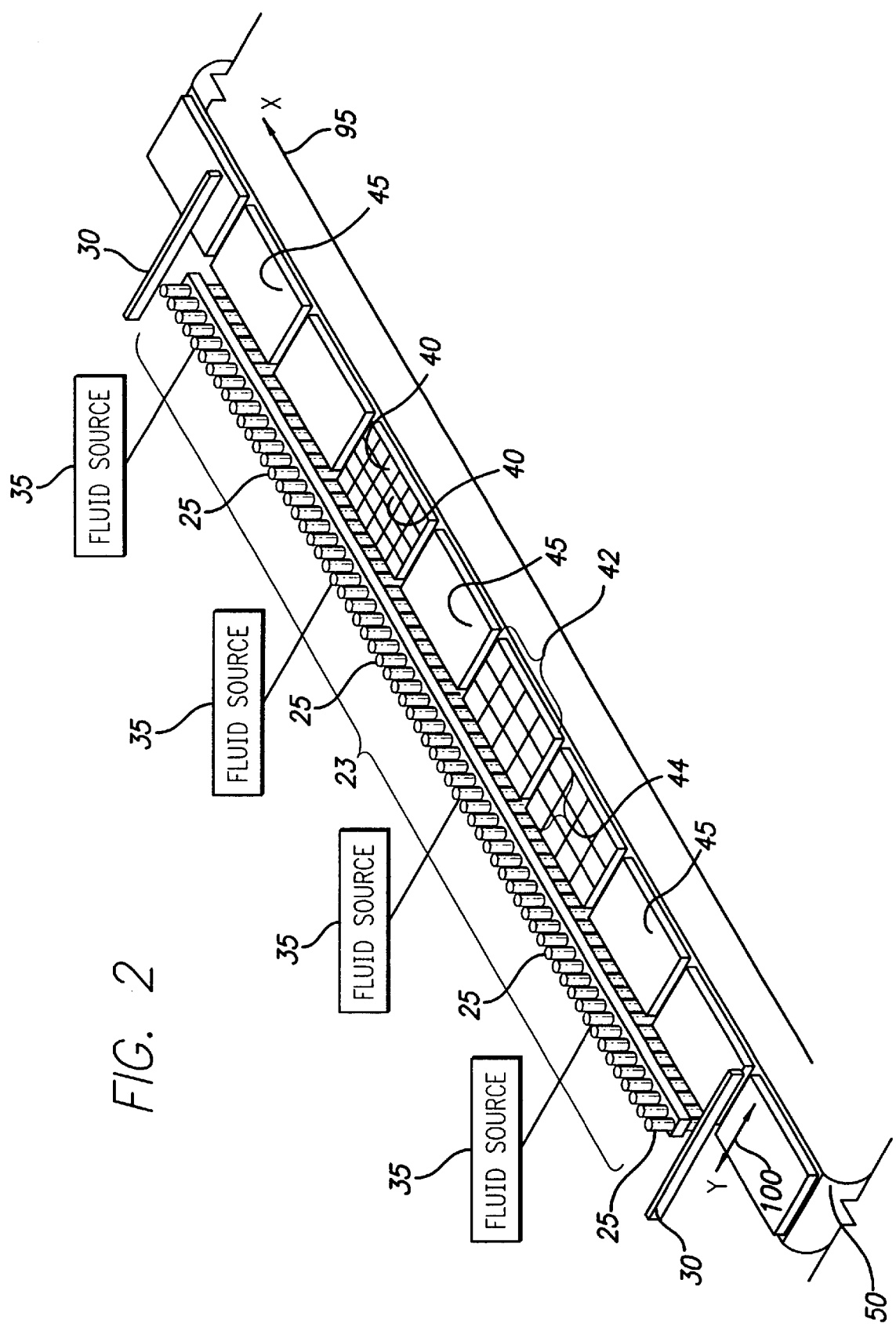
FIG. 2 is a perspective view of a plurality of multi-well vessels positioned underneath a tube array in accordance with the present invention.
Figure 3:
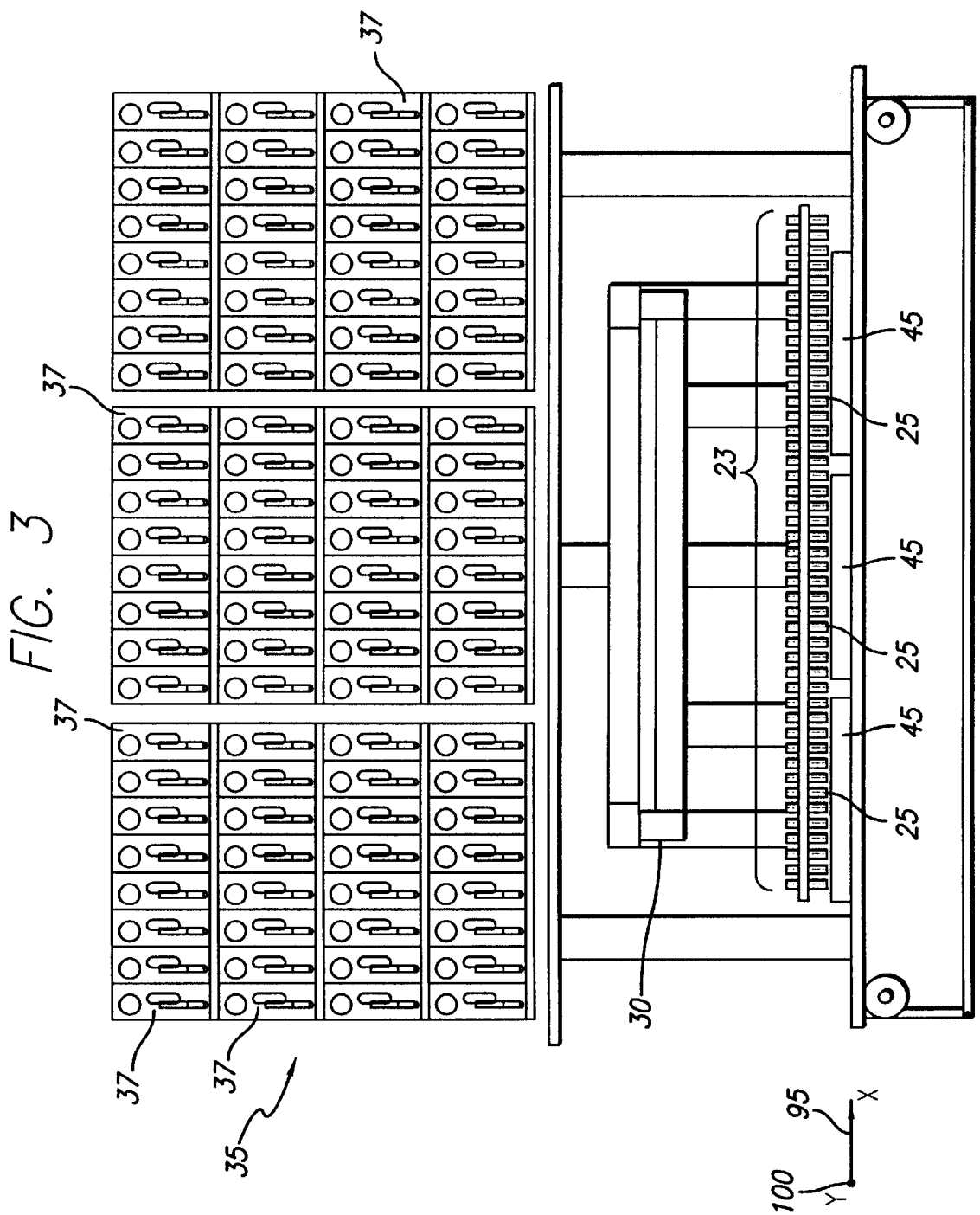
FIG. 3 is an elevation of a tube array and fluid source in accordance with the present invention.

Referring to FIGS. 2 and 3, tube transport 30 mounts the tube array so that the plurality of tubes are aligned with a conveyor 50. In a preferred embodiment the conveyor 50 provides for movement of multi-well vessels in the positive X-direction 95. The tube transport 30 is configured to move the tube array 23 in both the positive and negative Y-direction 100, which is substantially perpendicular to direction of movement provided by the conveyor 50. Although the conveyor 50 and the tube transport 30 are configured to provide relative movement between the tubes 25 and the vessels 45, other arrangements may be used for providing such relative movement. For example, either a conveyor or a tube transport may be individually constructed to provide both X- and Y-axis movement.

In a preferred embodiment, tube transport 30 communicates with controller 65 and is moved by electric motors, although other types of transport devices can be employed to move tube transport 30, such as pneumatic, hydraulic or other suitable devices.

A fluid source 35 comprises a plurality of fluid pumps 37 for pumping fluid to the tubes 25. The fluid pumps 37 are controlled by a plurality of pump control boxes 39, which are preferably operated by a controller 65. The controller 65 may be, for example, a general purpose computing device such as a commonly available PC which has been programmed to perform the steps required by the present invention. The controller 65 is operated through an operator interface 70 such as a touch-activated CRT. Other devices can be used to interface with the controller 65, such as a keyboard, or voice-activated system. Also, controller 65 may be a dedicated controller circuit or processor configured as an embedded controller, and may be locally present or accessed through a network, such as a local or wide area network.

In one embodiment, the fluid pumps 37 are solenoid valve dispensers that are connected to the tubes 25, which are positive displacement syringe pumps. The syringe pumps are configured to dispense very small amounts of fluid. For example, one embodiment of the present invention employs tubes 25 that dispense nanoliters or microliters of fluid, preferably about 1–10 nanoliters or microliters. In a preferred embodiment, the fluid source 35 comprises 96 solenoid valve dispensers each communicating with the 96 tubes 25.

When configured for protein crystallization growth, fluid pumps 37 are each coupled to a fluid source, with each fluid source being a "mother liquor" designed to facilitate growth of protein crystals. These mother liquors can be salts, buffers, detergents, organic chemicals, and other suitable fluids. Virtually any fluid can be dispensed by the fluid pumps 37 into tubes 25.

Referring to FIGS. 1 and 2, the tube array 23 is arranged to dispense fluid through the tubes 25 into individual wells 40 located in a multi-well plate or vessel 45. The multi-well plates 45 are dispensed from plate dispensers 55 onto a conveyor 50. The multi-well plates 45 are carried down the conveyor 50, and fluid is dispensed into the wells 40. The plates 45 are collected at the other end of the conveyor by plate receivers 60. Alternatively, the plates 45 can be delivered to a diving board 62 for delivery to another device or technician for further processing.

Illustrated in FIG. 1, plate dispensers 55 can store a plurality of vessels or plates 45 for dispensing onto conveyor 50. The plate dispensers 55 communicate with controller 65 to lower vessels 45 by a rack-and-pinion unit (not shown). In a similar arrangement, the plate receivers 60 can hold a plurality of plates or vessels 45. The vessels 45 are loaded into plate receivers 60 by an arrangement of posts which are rack-and-pinion driven (not shown). Other devices can be used to store and dispense vessels 45. For example, other robotic or manual arrangements may be employed.

Figure 4:
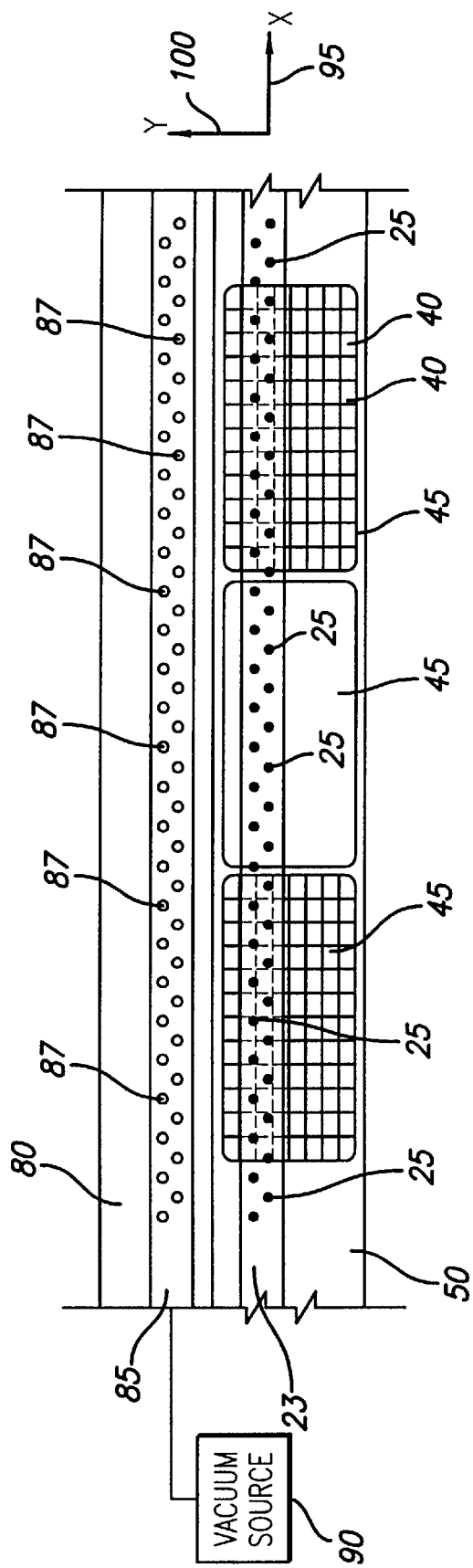
FIG. 4 is a plan view of a plurality of tubes positioned adjacent a multi-well vessel in accordance with the present invention.
Figure 6:
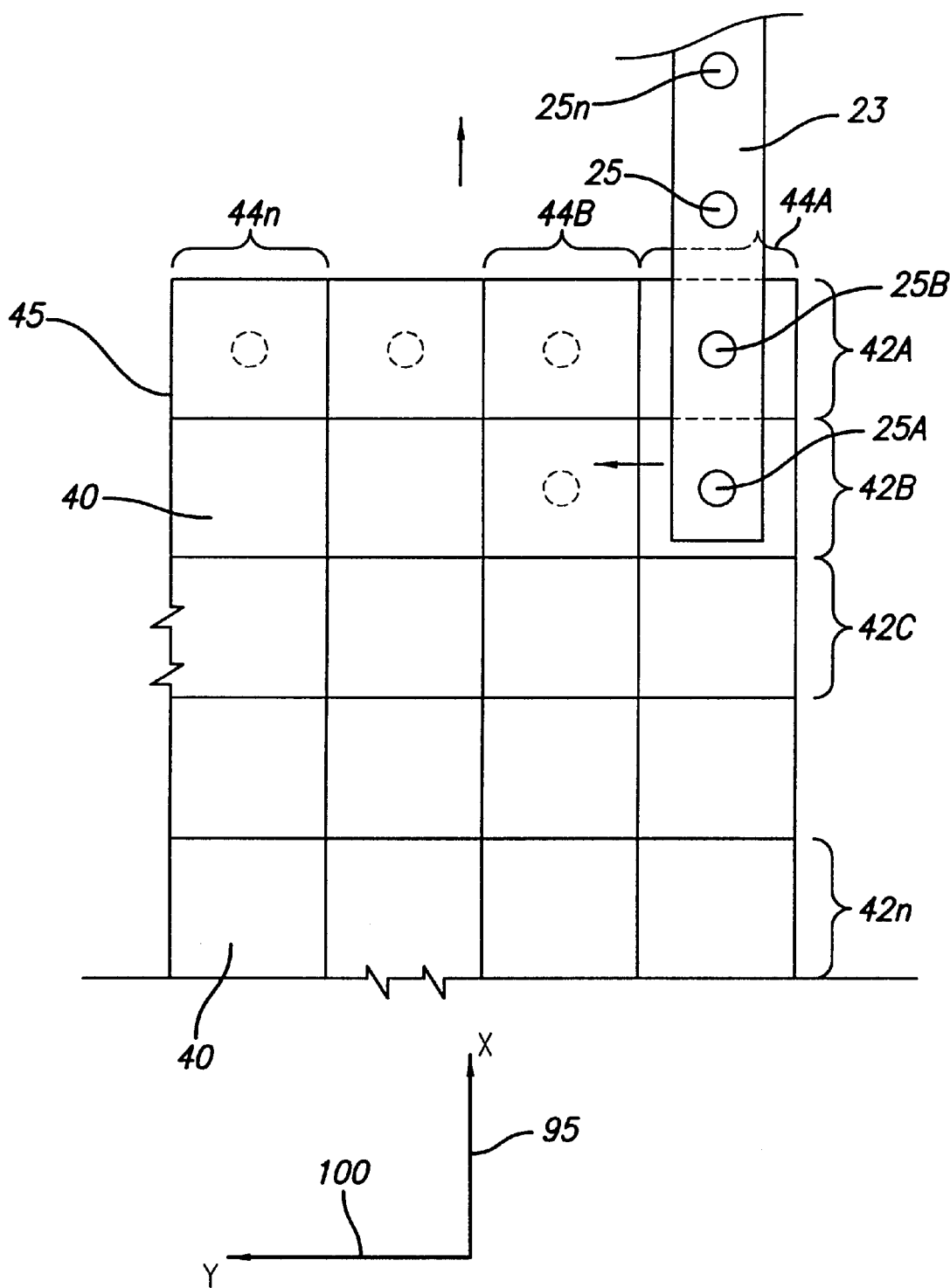
FIG. 6 is a plan view of a multi-well vessel positioned underneath a section of a tube array in accordance with the present invention.

In one embodiment, the present invention can be configured to dispense a multiplicity of different mother liquor fluid combinations into a plurality of wells located in vessels 45. In one embodiment, vessel 45 contains a total of 96 wells 40 arranged in eight columns and nine rows, as illustrated in FIGS. 2, 4 and 6. The twelve rows are parallel to the y-direction 100 and the columns of vessel 45 are parallel to the x-direction 95. More or fewer wells 40 may be contained in vessel 45.

One particular method of dispensing fluids for growing protein crystals employs four vessels 45, each vessel containing 96 wells 40 for a total of 384 wells. 96 different fluids are dispensed from the 96 tubes 25 mounted on the tube array 23. The combination of tubes 25 and their corresponding fluids dispense different combinations and concentrations of fluids so that each of the 384 wells contains a unique mixture of fluids. The specific unique mixture in each well is known by the controller and may be used for later process decisions or displayed on the operator interface 70. In this manner, a screen to determine the best combination and concentration of fluids for growing an optimum protein crystal can be quickly determined.

In a preferred embodiment, after dispensing the fluids into the 384 wells, protein crystals are grown and selected based on the quality of the crystal according to user-defined criteria. For example, the 16 "best" quality crystals are isolated and the specific combination and concentration of fluids used to grow those crystals are recalled by controller 65 and displayed using operator interface 70. Preferably, a "fine-screen" test is performed to optimize the concentration and combination of fluids for each of the 16 fluid combinations that resulted in the 16 best crystals.

During the fine-screen process of this preferred embodiment, 24 variations of each of the 16 fluid combinations are dispensed from the fluid dispensing tubes 25 into new vessel 45 wells 40. For example, if one of the 16 fluid combinations that resulted in a high-quality protein crystal comprised 5 percent of fluid A and 95 percent of fluid B, the corresponding fine screen would be composed of variations of the fluid combination of 5 percent of fluid A and 95 percent of fluid B. As an example, one of the 24 fine screen variations could be composed of 5.1 percent of fluid A and 94.8 percent of fluid B. Other variations could be 5.2 percent of fluid A and 94.9 percent of fluid B or 4.9 percent of fluid A and 95.1 percent of fluid B. In this manner, an optimized fluid combination and concentration can be determined for growing an optimum protein crystal.

II. Method for Dispensing Fluids

Figure 5:
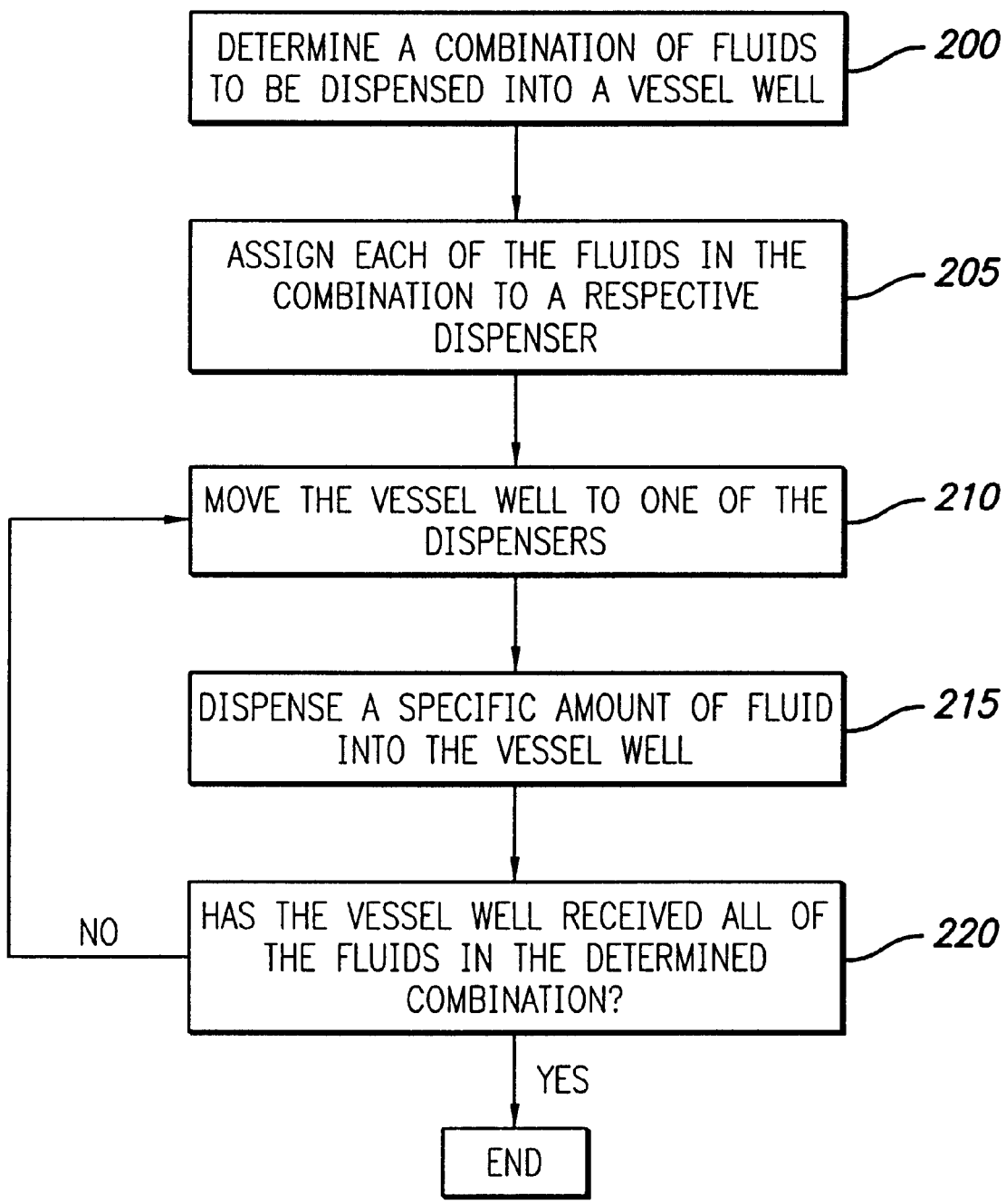
FIG. 5 is a flow-chart illustrating a method for dispensing a plurality of fluids in accordance with the present invention.

Referring to FIGS. 2, 4 and 5, one method and procedure for dispensing fluids or mother liquors into vessel 45 wells 40 are described. One embodiment of the present invention can dispense a multiplicity of mother liquor combinations and concentrations for later testing. This is useful because a range of fluid combinations and concentrations must be tested to determine which conditions will achieve a suitable protein crystal, since the specific criteria required to achieve a suitable protein crystal has not yet been determined for each protein in the human genome.

Referring to FIG. 5, in step 200, a combination of fluids to be dispensed into a vessel 45 well 40 is determined. In step 205, each of the fluids in the combination is assigned to a respective tube. In step 210, the vessel 45 well 40 is moved to one of the tubes. The fluid is then dispensed in a specific amount into the vessel 45 well 40 in step 215. Next, step 220 determines of whether the vessel has received all of the fluids of the specific fluid combination. If all of the required fluids have been dispensed into the vessel 45 well 40, the process ends. However, if additional fluids must be dispensed into the vessel 45 well 40, then the vessel 45 well 40 is moved to another tube 25, in step 210. Then step 215 and step 220 are performed as discussed, and this process is repeated until all of the necessary fluids have been dispensed into the specific vessel 45 well 40.

Referring to FIGS. 2 and 5, another procedure for dispensing mother liquors into specific vessel 45 well 40 will be described. Vessels 45 are placed on conveyor 50. Each vessel 45 comprises 12 rows 42 and 8 columns 44. Each well 40 and each vessel 45 has a column 42 height of about 9 millimeters and a row width of about 9 millimeters. Other vessels 45 can be employed having different numbers of wells 40 and different well 40 dimensions.

After the vessel 45 is placed on the conveyor 50 the conveyor moves the vessel 45 in 9 millimeter increments in the X-direction 95. Tube array 23 containing 96 tubes 25 is moved by tube transport 30 in the Y-direction 100. Illustrated in FIG. 6, controller 65 aligns the first tube 25A of the tube array 23 over a first well 40 in a first row 42A, first column 44A. As discussed above and illustrated in FIG. 5, the controller determines whether or not a fluid must be dispensed into that specific vessel 45 well 40. If the controller orders fluid to be dispensed into that specific well 40, the fluid is dispensed through the first tube 25A.

The tube array 23 is then moved by tube transport 30 over one column (i.e., 9 millimeters). This positions the first tube 25A over a second well 40 in the first row 42A, second column 44B. Again, controller 65 determines whether or not fluid is to be dispensed into the second well 40. Once the fluid has been dispensed, if necessary, the tube transport 30 moves the tube array 23 a distance of 9 millimeters to the next column 44C and positions the first tube 25A over a third well 40. This process is repeated until the first tube 25A has been positioned over each well 40 in the first row 42A of the plate 45. Conveyor 50 then moves the plate 45 in the X-direction 95 9 millimeters, positioning the first tube 25A over the first well in the second row 42B.

Illustrated in FIG. 6, first tube 25A coupled to tube array 23 and second tube 25B also coupled to tube array 23 are positioned over the first well 40 of the first two rows 42A and 42B. The procedure described in step 210 of FIG. 5 is now repeated for the first well 40 in row 42B as well as the first well of row 42A. Because two tubes 25A and 25B are positioned over two wells 40, two different fluids can be dispensed simultaneously, if necessary, depending upon the combination of fluids to be dispensed into each well 40. Once the controller has determined if a fluid is to be dispensed into each well and that dispensing has occurred, the tube transport 30 moves the tube array 23 in the Y-direction 100 to position the first tube 25A and second tube 25B over the next column 44B in the plate 45. The dispensing of fluids then commences if necessary for that well 40. In this manner, appropriate fluids can be dispensed in the appropriate combination and concentration into each well 40 of each vessel 45.

Referring to FIGS. 2 and 4, as the vessels 45 progress down the conveyor 50 and are exposed to more tubes 25 and the tube array 23, the controller can dispense up to 96 fluids substantially simultaneously if necessary. In this manner, an extremely high throughput of fluid combinations can be achieved in the wells 40 of each vessel 45. The rate of fluids that can be dispensed by the present invention is unachievable by human technicians and allows any for an extremely high number of combinations of fluids to be dispensed. In addition, each combination and concentration of fluids in each well 40 can be recalled from the operator interface 70, and can be repeated with repeatable accuracy due to the automated process performed by the present invention.

The arrangement of tubes need not be in a linear arrangement as illustrated in FIG. 2. For example, shown in FIG. 4, the tubes 25 can be arranged in a staggered configuration or any other suitable configuration.

Referring to FIG. 4, the tubes 25 can be periodically rinsed and dried so that the concentrations of fluids dispensed through the tubes remain consistent. Tube transport 30 positions the tube array 23 over the tube bath 80 that contains a suitable tube rinse, such as ethanol or ionized water or any other suitable rinsing fluid. The tubes are immersed in the rinse and then the tube array 23 is moved by the tube transport 30 to the tube dryer 85 that is connected to a vacuum source 90. The tube dryer 85 includes tube holes 87 into which the tubes 25 are inserted by the tube transport 30. The vacuum source 90 is turned on by the controller 65, drying the tubes 25.

One skilled in the art will appreciate that the present invention can be practiced by other than the preferred embodiments which are presented in this description for purposes of illustration and not of limitation, and the present invention is limited only by the claims that follow. For example, features of the methods and devices described in International Patent Publication WO 00/78445, published Dec. 28, 2000, incorporated herein by reference in its entirety including any drawings or figures, can be used in conjunction with the methods and devices of the present invention. It is noted that equivalents for the particular embodiments discussed in this description may practice the invention as well.

What is claimed is:

1. An apparatus for preparing fluid mixtures in a plurality of multi-well vessels, each of the multi-well vessels having a plurality of wells, the apparatus comprising:
   a multi-well vessel moving apparatus configured to receive and move the plurality of multi-well vessels in a first direction;
   a plurality of tubes, each tube configured to dispense a fluid into individual wells of the multi-well vessels, where the tubes have a footprint in the column direction, where each of the multi-well vessels has a footprint in the column direction, where the footprint of the tubes in the column direction is longer than the footprint of any single one of the multi-well vessels in the column direction;
   a tube mover configured to move the plurality of tubes in a second direction; and
   a controller communicating with the vessel moving apparatus, the plurality of tubes and the tube mover, the controller programmed to selectively move the multi-well vessels and the tube mover and dispense fluid into individual wells of the multi-well vessels.

2. The apparatus for preparing fluid mixtures according to claim 1, further comprising a plurality of fluid containers, wherein each fluid container is in fluid communication with a tube.

3. The apparatus for preparing fluid mixtures according to claim 1, wherein adjacent tubes dispense different fluids.

4. The apparatus for preparing fluid mixtures according to claim 1, wherein the vessel moving apparatus comprises a conveyer belt.

5. The apparatus for preparing fluid mixtures according to claim 1, wherein the plurality of tubes is arranged so that there is only one tube in a row direction.

6. The apparatus for preparing fluid mixtures according to claim 1, wherein the plurality of tubes is arranged so that there are at least 9 tubes in the column direction.

7. The apparatus for preparing fluid mixtures according to claim 1, wherein the plurality of tubes is arranged so that there are at least 13 tubes in the column direction.

8. The apparatus for preparing fluid mixtures according to claim 1, wherein the plurality of tubes is arranged so that there are at least 17 tubes in the column direction.

9. The apparatus for preparing fluid mixtures according to claim 1, wherein the plurality of tubes is arranged so that there are at least 25 tubes in the column direction.

10. The apparatus for preparing fluid mixtures according to claim 1, wherein the plurality of tubes is arranged so that there are at least 33 tubes in the column direction.

11. The apparatus for preparing fluid mixtures according to claim 1, wherein the controller comprises computer executable logic for causing the plurality of tubes to be sequentially moved across entire rows of the multi-well vessels before the controller sequentially advances the multi-well vessels to a next row position.

12. The apparatus for preparing fluid mixtures according to claim 1, wherein the first direction comprises the column direction.

13. The apparatus for preparing fluid mixtures according to claim 1, wherein the second direction comprises a row direction.

14. The apparatus for preparing fluid mixtures according to claim 1, wherein the controller comprises computer executable logic for causing the multi-well vessels to move to a different row position before causing the plurality of tubes to move to a different column position.

15. The apparatus for preparing fluid mixtures according to claim 1, wherein the controller comprises computer executable logic for causing the plurality of tubes to be positioned at a first or last column position when the multi-well vessels are moved to a different row position.

16. The apparatus for preparing fluid mixtures according to claim 1, wherein a distance between adjacent wells of the multi-well vessels in a row direction is about 9 mm.

17. The apparatus for preparing fluid mixtures according to claim 1, wherein a distance between adjacent wells of the multi-well vessels in the column direction is about 9 mm.

18. The apparatus for preparing fluid mixtures according to claim 1, wherein each of the multi-well vessels has at least 48 wells.

19. The apparatus for preparing fluid mixtures according to claim 1, wherein the first and second directions are orthogonal to one another.

20. The apparatus for preparing fluid mixtures according to claim 1, wherein a plurality of fluids is dispensed substantially simultaneously into a plurality of wells in the multi-well vessels from the plurality of tubes.

21. The apparatus for preparing fluid mixtures according to claim 1, wherein the plurality of tubes is configured so that at least two multi-well vessels can be positioned beneath the plurality of tubes at the same time.

22. The apparatus for preparing fluid mixtures according to claim 1, wherein the plurality of tubes is configured so that at least three multi-well vessels can be positioned beneath the plurality of tubes at the same time.

23. The apparatus for preparing fluid mixtures according to claim 1, wherein the plurality of tubes is configured so that at least four multi-well vessels can be positioned beneath the plurality of tubes at the same time.

24. The apparatus for preparing fluid mixtures according to claim 1, wherein the plurality of tubes is configured so that fluids can be delivered to at least two multi-well vessels at the same time.

25. The apparatus for preparing fluid mixtures according to claim 1, wherein the plurality of tubes is configured so that fluids can be delivered to at least three multi-well vessels at the same time.

26. The apparatus for preparing fluid mixtures according to claim 1, wherein the plurality of tubes is configured so that fluids can be delivered to at least four multi-well vessels at the same time.

27. The apparatus for preparing fluid mixtures according to claim 1, wherein fluids can be delivered from each of the plurality of tubes at the same time.

28. The apparatus for preparing fluid mixtures according to claim 1, wherein the vessel moving apparatus comprises a length of at least n of the multi-well vessels, wherein n is the number of multi-well vessels, wherein each of the multi-well vessels has m wells, wherein m is the number of wells, and wherein the apparatus processes one of the multi-well vessels every m dispensings even though each of the multi-well vessels is in the apparatus for n times m dispensings.

29. The apparatus for preparing fluid mixtures according to claim 1, wherein the vessel moving apparatus comprises a length of at least two multi-well vessels.

30. The apparatus for preparing fluid mixtures according to claim 1, wherein the vessel moving apparatus comprises a length of at least three multi-well vessels.

31. The apparatus for preparing fluid mixtures according to claim 1, wherein the vessel moving apparatus comprises a length of at least four multi-well vessels.

32. The apparatus for preparing fluid mixtures according to claim 1, further comprising a plurality of fluid containers, wherein each fluid container is in fluid communication with a different tube.

33. The apparatus for preparing fluid mixtures according to claim 3, wherein each fluid container holds a stock solution, and the fluid dispensed into a well is received from multiple fluid containers.

34. The apparatus for preparing fluid mixtures according to claim 3, wherein each fluid container holds a predetermined liquid mixture of stock solutions, and the fluid dispensed into each well is received from only one fluid container.

35. A method for automatically preparing a mixture in a well of a multi-well holder, said method comprising the steps of:
    moving the multi-well holder so that at least one of the wells is positioned below a fluid dispensing device, where each of the fluid dispensing devices has a footprint in the column direction, where each of a plurality of multi-well holders has a footprint in the column direction, where the footprint of the fluid dispensing devices in the column direction is longer than the footprint of any single one of the multi-well holders in the column direction;
    dispensing fluid from the fluid dispensing device into the well; and
    repeatedly moving the multi-well holders so that the well is positioned below a next fluid dispensing device and dispensing fluid from the next fluid dispensing device into the well until a predetermined mixture is prepared.

36. The method of claim 35, further comprising dispensing different fluids from adjacent dispensing devices.

37. The method of claim 35, wherein an array comprises the fluid dispensing devices.

38. The method of claim 35, wherein the fluid dispensing devices are configured so that at least two multi-well holders can be beneath the fluid dispensing devices at the same time.

39. The method of claim 35, wherein the fluid dispensing devices are configured so that at least three multi-well holders can be beneath the fluid dispensing devices at the same time.

40. The method of claim 35, wherein the fluid dispensing devices are configured so that at least four multi-well holders can be beneath the fluid dispensing devices at the same time.

41. The method of claim 35, wherein the fluid dispensing devices are configured to deliver fluids to at least two multi-well holders at the same time.

42. The method of claim 35, wherein the fluid dispensing devices are configured to deliver fluids to at least three multi-well holders at the same time.

43. The method of claim 35, wherein the fluid dispensing devices are configured to deliver fluids to at least four multi-well holders at the same time.

44. The method of claim 35, wherein the fluid dispensing devices are configured to deliver fluids at the same time.

45. The method of claim 35, wherein each multi-well holder has at least 96 wells.

46. The method of claim 35, wherein multiple fluids are dispensed substantially simultaneously from the dispensing devices to the multi-well holders.

47. The method of claim 35, wherein the multi-well holders are on a moving element that has a length of at least n of the multi-well holders, wherein n is the number of the multi-well holders, wherein each of the multi-well holders has m wells, wherein m is the number of wells, wherein the method processes one of the multi-well holders every m dispensings even though the method involves n times m dispensings.

48. The method of claim 47, wherein the multi-well holders are on a moving element that has a length of at least two multi-well holders.

49. The method of claim 47, wherein the multi-well holders are on a moving element that has a length of at least three multi-well holders.

50. The method of claim 47, wherein the multi-well holders are on a moving element that has a length of at least four multi-well holders.

51. The method of claim 35, wherein each fluid dispensing device is in fluid communication with a different fluid container.

52. The method of claim 35 or 51, wherein a controller directs dispensing of the fluid from the fluid dispensing devices.

53. The method of claim 52, wherein the controller directs the delivery of the fluids from each of at least eight fluid containers to each of at least two multi-well holders.

54. The method of claim 52, wherein the controller directs the delivery of the fluids from each of at least eight fluid containers to each of at least three multi-well holders.

55. The method of claim 52, wherein the controller directs the delivery of the fluids from each of at least eight fluid containers to each of at least four multi-well holders.

56. The method of claim 35, further comprising moving the fluid dispensing devices in a row direction so that one or more wells in the row direction are positioned below one or more fluid dispensing devices.

57. The method of claim 56, wherein the step of moving the fluid dispensing devices in the row direction is performed prior to the repeatedly moving step.

58. The method of claim 56, further comprising dispensing fluid from the fluid dispensing devices into selected wells in the row direction.

59. The method of claim 58, further comprising continuing to move the fluid dispensing devices and to dispense the fluid into the selected wells until at least one fluid dispensing device has been positioned directly above each of the wells in a row.

60. The method of claim 35 or 56, further comprising:
    advancing the multi-well holder to a next row position; and
    moving the fluid dispensing devices and dispensing fluid into selected wells while the selected wells are positioned below the fluid dispensing devices in the next row position.

* * * * *